(12) United States Patent
Bolton et al.

(10) Patent No.: US 7,597,906 B2
(45) Date of Patent: *Oct. 6, 2009

(54) APOPTOSIS-MIMICKING SYNTHETIC ENTITIES AND USE THEREOF IN MEDICAL TREATMENT

(75) Inventors: Anthony E. Bolton, Dublin (IE); Arkady Mandel, Mississauga (CA)

(73) Assignee: Vasogen Ireland Limited (IE)

( * ) Notice: Subject to any disclaimer, the term of this patent is extended or adjusted under 35 U.S.C. 154(b) by 0 days.

This patent is subject to a terminal disclaimer.

(21) Appl. No.: 11/688,167

(22) Filed: Mar. 19, 2007

(65) Prior Publication Data

US 2007/0224256 A1    Sep. 27, 2007

Related U.S. Application Data

(62) Division of application No. 11/039,469, filed on Jan. 19, 2005, which is a division of application No. 09/957,698, filed on Sep. 18, 2001, now Pat. No. 6,953,591.

(30) Foreign Application Priority Data

Sep. 18, 2000 (CA) ............................. 2319928

(51) Int. Cl.
*A61K 9/127* (2006.01)
*A01V 25/00* (2006.01)
(52) U.S. Cl. .............................. 424/450; 514/885
(58) Field of Classification Search ............... None
See application file for complete search history.

(56) References Cited

U.S. PATENT DOCUMENTS

| | | | |
|---|---|---|---|
| 4,595,680 | A | 6/1986 | Della Valle et al. |
| 5,470,578 | A | 11/1995 | Aoki et al. |
| 5,770,234 | A | 6/1998 | Gristina et al. |
| 5,948,756 | A | 9/1999 | Barenholz et al. |
| 6,290,987 | B1 | 9/2001 | Modi |
| 6,312,719 | B1 | 11/2001 | Hope et al. |
| 6,630,313 | B2 | 10/2003 | Fadok et al. |
| 2002/0044924 | A1* | 4/2002 | Bolton et al. ............ 424/93.21 |
| 2005/0147660 | A1* | 7/2005 | Bolton et al. ............ 424/450 |
| 2007/0087010 | A1* | 4/2007 | Bolton et al. ............ 424/184.1 |
| 2008/0124386 | A1* | 5/2008 | Bolton et al. ............ 424/450 |
| 2008/0131416 | A1* | 6/2008 | Bolton et al. ............ 424/93.71 |

FOREIGN PATENT DOCUMENTS

| | | |
|---|---|---|
| CA | 2063039 | 9/1992 |
| DE | 41 17 629 | 12/1992 |
| EP | 0 315 349 | 5/1989 |
| EP | 0 505 817 | 9/1992 |
| WO | WO 92/02226 | 2/1992 |
| WO | WO 95/23592 | 9/1995 |
| WO | WO 01/43750 | 6/2001 |
| WO | WO 01/66875 | 9/2001 |

OTHER PUBLICATIONS

Aramaki, et al. "Liposomes as Immunomodulator—Inhibitory Effect of Liposomes on NO Production from Macrophases" *Biol. Pharm. Bull.*, 2000 pp. 1267-1274, vol. 23, No. 11.
Bennett et al. "Binding and Phagocytosis of Apoptotic Vascular Smooth Muscle Cells Is Mediated in Part by Exposure of Phosphatidyserine" *Circulation Research*, 1995, pp. 1136-1142, vol. 77, n o. 6.
Bliss et al. "A synapic model of memory: long-term potentiation in the hippocampus" *Nature* 1993, pp. 31-39, vol. 361.
Daemen et al. "Different Intrapepatic Distribution of Phosphatidylglycerol and Phosphatidylserine Liposomes in the Rat" *Hepatology*, 1997, pp. 416-423, vol. 26, No. 2.
Delwaide et al. "Double-blind randomized controlled study of phosphatidylserine in senile demented patients" *Acta neurol. Scand.* 1986, pp. 136-140, vol. 73.
Emoto et al. "Short Note—Exposure of Phosphatidylethanolamine on the Surface of Apoptotic Cells" *Experimental Cell Research* 1997, pp. 430-434, vol. 232.
Fadok et al. "Macrophages That Have Ingested Apoptotic Cells In Vitro Inhibit Proinflammatory Cytokine Production Through Autocrine/Paracrine Mechanisms Involving TGF-β, PGE2, and PAF" *J. Clin. Invest.* 1998 pp. 890-898, vol. 101, No. 4.
Fadok et al. "Exposure fo Phosphatidylserine on the Surface of Apoptotic Lymphocytes Triggers Specific Recognition and Removal by Macrophages" *The Journal of Immunology* 1992, pp. 2207-2216, vol. 148, No. 7.
Fdok et al. "A receptor for phosphatidylserine-specific clearance of apoptotic cells" *Nature* 2000, pp. 85-90, vol. 405.
Fadok et al. "Loss of Phospholipid Asymmetry and Surface Exposure of Phosphatidylserine Is Required for Phagocytosis of Apoptotic Cells by Macrophages and Fibroblasts" *The Journal of Biological Chemistry* 2001, pp. 1071-1077, vol. 276, No. 2.
Griffin et al. "Brain interleukin 1 and S-100 immunoreactivity are elevated in Down Syndrome and Alzheimer disease" *Proc. Natl. Acad. Sci.* 1989, pp. 7611-7615, vol. 86.
Kerr et al. "Apoptosis: A basic biological phenomenon with wide-ranging implications in tissue kinetics" *Br. J. Cancer*, 1972, pp. 239-257, vol. 26.
Kornbluth et al. "The immunological potential of apoptotic debris produced by tumor cells and during HIV infection" *Immunology Letters*, 1994, pp. 125-132, vol. 43.
Mogi et al. "Interleukin (IL)-1β, IL-2, IL-4, IL-6 and transforming growth factor-α levels are elevated in ventricular cerebrospinal fluid in juvenile parkinsonism and Parkinson's disease" *Neuroscience Letters* 1996, pp. 13-16, vol. 211.
Monastra et al. "Phosphatidylserine, a putative inhibitor of tumor necrosis factor, prevents autoimmune demyelination" *Neurology* 1993, pp. 153-163, vol. 43.

(Continued)

*Primary Examiner*—Michail A Belyavskyi
(74) *Attorney, Agent, or Firm*—Foley & Lardner LLP (57) ABSTRACT

Synthetic and semisythetic bodies having a three-dimensional structure, sized and shaped to resemble apoptotic cells and apoptotic bodies, and having phosphatidyl serine (PS) molecules on the surface thereof, are administered to a patient, to alleviate a variety of disorders such as T-cell mediated disorders (autoimmune conditions). The bodies are believed to trigger and apoptosis-like mechanism in the patient.

5 Claims, 6 Drawing Sheets

OTHER PUBLICATIONS

Murray et al. "Evidence That Increased Hippocampal Expression of the Cytokine Interleukin-1β Is a Common Trigger for Age—and Stress-Induced Impairments in Long-term Potentiation" *The Journal of Neuroscience* 1998, pp. 2974-2981, vol. 18, No. 8.

Miyamoto et al. "Effects of Differently Composed Liposomes on Pulmonary Arterial Pressure in Sheep —Involvement of Pulmonary Intravascular Macrophages" *Nihon Kyobu Skikkan Gakkai Zasshi* 1991, pp. 1268-1274 [English language abstract].

Nassander et al. "Liposomes" *Biodegradable Polymers as drug Delivery Systems* (M. Chasin and R. Langer, eds.) Marcel Dekker Inc., New York, NY 1990, pp. 261-338, Chapter 8.

Palatini et al. "Pharmacokinetic characterization of phosphatidylserine liposomes in the rat" *Br. J. Pharmacol.* 1991, pp. 345-350, vol. 102.

Shiratsuchi et al. "Phosphatidylserine-Mediated Phagocytosis of anticancer Drug-Treated Cells by Macrophages" *J. Biochem.* 1999, pp. 1101-1106, vol. 26, No. 6.

Zanotti et al. "Chronic phosphatidylserine treatment improves spatial memory and passive avoidance in aged rats" *Psychopharmacology* 1989, pp. 316-321, vol. 99.

Aramaki et al. "Inhibitory Effects of negatively Charged Liposomes on Nitric Oxide Production from Macrophages Stimulated by LPS" *Biochemical Piophysical Research Communications*, 1996, pp. 1-6, vol. 220.

Bruni et al. "Pharmacological effects of phosphatidylserine liposomes" *Nature* 260:331-333 (1976).

Cenacchi et al. "Cognitive decline in the elderly: A double-blind, placebo-controlled multicenter study on efficacy of phosphatidylserine administration" *Aging Clin. Exp. Res.* 5:123-133 (1993).

Engel et al. "Double-blind cross-over study of phosphatidylserine vs. placebo in patients wit early dementia of the Alzheimer type" *Eur. Neuropsychopharmacology* 2:149-155 (1992).

Miller, et al. "Is variant angina the coronary manifestation of a generalized vasospastic disorder?" *The New England Journal of Medicine* 304(13)763-766 (1981).

Oussoren et al. "Lymphatic uptake and boidistribution of liposomes after subcutaneous injection. II. Influence of liposomal size, lipid composition and lipid dose" *Biochimica et Biophysica Acta.* 1328:261-272 (1997).

Scott, et al. "Phagocytosis and clearance of apoptotic cells is mediated by MER" *Nature* 411:207-211 (2001).

Van Noort et al. "International Review of Cytology", 1998.

Girolomoni et al. (1993) "Phosphatidylserine Enhances the Ability of Epidermal Langerhans Cells to Induce Contact Hypersensitivity" *The Journal of Immunology* 150:4236-4243.

* cited by examiner

APOPTOSIS-MIMICKING SYNTHETIC ENTITIES AND USE THEREOF IN MEDICAL TREATMENT

CROSS-REFERENCE TO RELATED APPLICATION

This application is a divisional of U.S. application Ser. No. 11/039,469, filed Jan. 19, 2005, which is a divisional of U.S. application Ser. No. 09/957,698, filed Sep. 18, 2001, now U.S. Pat. No. 6,953,591, issued on Oct. 11, 2005. This application also claims priority to Canadian Application Serial No. 2,319,928, filed on Sep. 18, 2000.

FIELD OF THE INVENTION

This invention relates to synthetic and semi-synthetic compositions having biochemical activity, and to the uses thereof in the treatment and/or prophylaxis of various disorders in mammalian patients. More particularly, it relates to preparation and use of synthetic and semi-synthetic bodies which can mimic the process of cell apoptosis after introduction into the body of a patient, to produce beneficial effects.

BACKGROUND OF THE INVENTION

The following documents are cited herein:

1. Kerr, J. F. R., Wyllie A. H., Currie, A. R. (1992), "Apoptosis: a basic biological phenomenon with wide-ranging implications in tissue kinetics." British Journal of Cancer 26: 239-257;
2. Fadok (1998) J. Clin. Invest., 101, 890-898;
3. Fadok V. A., Voelker D. P., Campbell P. A., Cohen, J. J., Bratton, D. L., Henson, P. M. (1992), "Exposure of phosphatidylserine on the surface of apoptotic lymphocytes triggers specific recognition and removal by macrophages." Journal of Immunology 148:2207-2216;
4. Fadok V. A., Bratton, D. L., Rose, D. M., Pearson, A., Exekewitz R. A. B., Henson, P. M. (2000), "A receptor for phosphatidylserine-specific clearance of apoptotic cells," Nature 405:85-90;
5. Monastra et al. Neurology (1993) 48:153-163;
6. Zanotti et al., 1989;
7. Delwaide et al., (1986) Acta Neurol. Scand.; 73: 136-140.
8. Yechezkel Barenholz and Daan J. A. Chromeline, Liposomes as Pharmaceutical Dosage Forms, and literature cited therein, for example New, R. C., "Liposomes: A Practical Approach," IRL Press at Oxford University Press, Oxford, England (1990), and Nassander, U. K., et al., In: "Biodegradable Polymers as Drug Delivery Systems" (M. Chasin and R. Langer, eds.) Marcel Dekker Inc., New York 1990, pages 261-338;
9. Griffin W S T, Stanley, L. C., Ling, C., White, L., Macleod, V. Perrot L. H J., White, C. L., Araoz, C., (1989), Brain interleukin 1 and S-100 immunoreactivity are elevated in Down's syndrome and Alzheimer's disease, Proceedings of the National Academy of Sciences USA 86: 7611-7615;
10. Mogi M., Harada, M., Narabayashi, H., Inagaki, H., Minami, M., Nagatsu T., (1996) "Interleukin (IL)-1 beta, IL-1, IL-4, IL-6 and transforming growth factor-alpha levels are elevated in ventricular cerebrospinal fluid in juvenile parkinsonism and Parkinson's disease," Neuroscience Letters 211: 13-16;
11. Murray, C. A., Lynch, M. A., (1998) "Evidence that increase hippocampal expression of the cytokine interleukin-1.beta. is a common trigger for age and tress-induced impairments in long-term potentiation," Journal of Neuroscience 18:2974-2981;
12. Bliss, T. V. P., Collinridge, G. L., (1993) "A synaptic model of memory: long-term potentiation in the hippocampus," Nature 361:31-39.

Two mechanisms of cell death in the body are recognized, necrosis and apoptosis. Apoptosis is the process of programmed cell death, described by Kerr et al. (1992) by which steady-state levels of the various organ systems and tissues in the body are maintained as continuous cell division is balanced by cell death. Cells undergoing apoptosis often exhibit distinct morphological changes such as pronounced decrease in cell volume, modification of the cytoskeletons resulting in pronounced membrane blebbing, a condensation of the chromatin, and degradation of the DNA into oligonucleosomal fragments. Following these morphological changes, an apoptotic cell may break up into a number of small fragments known as apoptotic bodies, consisting essentially of membrane-bound bodies containing intact organelles, chromatin etc. Apoptotic cells and apoptotic bodies are normally rapidly removed from the body by phagocytosis principally by macrophages and dendritic cells, before they can become lysed and release their potentially pro-inflammatory intracellular contents.

Macrophages which have ingested apoptotic cells and/or apoptotic bodies (e.g. phagocytosis) appear to inhibit pro-inflammatory cytokine production (Fadok et al., 1998) and thus may down-regulate a Th-1 response in a patient's immune system. Such down-regulation can also be achieved following injection of apoptotic cells or bodies, or following injection of cells susceptible to accelerated apoptosis.

During apoptosis, phosphatidylserine becomes exposed externally on the cell membrane (Fadok et al. (1992)) and this exposed phosphatidylserine binds to specific receptors to mediate the uptake and clearance of apoptotic cells in mammals (Fadok et al (2000)). The surface expression of phosphatidylserine on cells is a recognized method of identification of apoptotic cells.

Monastra et al. (1993) describe that the administration of phospholipid phosphatidylserine (PS) derived from bovine cortex (BC-PS) may have an effect on adoptively transferred Experimental Autoimmune Encephalomyelitis (EAE) in SJL/J mice. However, an extremely high dose of BC-PS, 30 mg/kg, was injected intraperitoneally on a daily basis. An equivalent dose of liposomes given to a human (greater than 2 grams per average individual) would be potentially toxic, expensive and therefore impractical and undesirable. Such quantities would be active, if at all, as drugs, and would be too large to act as immune system modifiers.

Oral administration of PS has been used both in animal models to improve spatial memory, in amounts of 50 mg/day (Zanotti et al., 1989), and in humans to treat Alzheimer's disease, in amounts of 300 mg/day (Delwaide et al., 1986) and showed statistically significant improvements in PS treated subjects as compared with placebo.

SUMMARY OF THE INVENTION

This invention is directed to the surprising discovery that PS-carrying bodies may be used to treat a number of diseases.

In particular, it is directed to a method for treating a T-cell function-mediated disorder comprising administering to a mammalian patient a non-toxic effective T-cell function-mediated disorder-treating amount of PS-carrying bodies wherein the progression of the T-cell function-mediated disorder is inhibited and/or symptoms of the disorder are reduced.

It is further directed to a method for treating an inflammatory disorder comprising administering to a mammalian patient a non-toxic effective inflammatory disorder-treating amount of PS-carrying bodies, wherein the progression of the inflammatory disorder are inhibited and/or symptoms of the disorder are reduced.

Yet another embodiment of this invention is a method for treating an endothelial function disorder comprising administering to a mammalian patient a non-toxic effective endothelial function disorder-treating amount of PS-carrying bodies, wherein the progression of the endothelial function disorder are inhibited and/or symptoms of the disorder are reduced.

Another embodiment is a method for treating an immune system disorder characterized by an inappropriate cytokine expression comprising administering to a mammalian patient a non-toxic effective inappropriate cytokine expression-treating amount of PS-carrying bodies, wherein the progression of the disorder are inhibited and/or symptoms of the disorder are reduced.

This invention is also directed to pharmaceutical compositions comprising pharmaceutically acceptable biocompatible synthetic or semi-synthetic bodies for administration to a mammalian patient and a pharmaceutically acceptable carrier, wherein at least a portion of said bodies have a conformation and size corresponding to mammalian apoptotic bodies wherein the surface of said bodies have been modified to contain a plurality of ligands for one or more phosphatidylserine receptors; which bodies are capable of binding to a phosphatidylserine receptor on an antigen presenting cell when administered to the mammalian patient. The biocompatible synthetic body may be a liposome.

Yet another embodiment of this invention is pharmaceutical compositions comprising a pharmaceutical carrier and biocompatible non-liposomal synthetic bodies for administration to a mammalian patient wherein the non-liposomal biocompatible synthetic bodies comprise pharmaceutically acceptable bodies have a conformation and size corresponding to mammalian apoptotic bodies wherein the surface of said pharmaceutically acceptable body has been modified to contain a plurality of ligands for one or more phosphatidylserine receptors; which biocompatible synthetic bodies are capable of binding to a phosphatidylserine receptor on an antigen presenting cell when administered to the mammalian patient The biocompatible non-liposomal synthetic bodies may be selected from polysaccharides such as hydroxyethylcellulose, hydroxethyl starch, and agarose, polyethylene glycol, polyvinylprrolidone, polystyrene and a wide range of other natural, semi-synthetic and synthetic materials.

In another embodiment, this invention is directed to lyophilized or freeze-dried PS-carrying bodies and kits of parts containing lyophilized or freeze-dried PS-carrying bodies and a pharmaceutically acceptable carrier.

DESCRIPTION OF THE INVENTION

According to the present invention, synthetic and semi-synthetic bodies which have the property of mimicking in vivo apoptotic cells and/or apoptotic bodies in that they are taken up by cells of the patient's immune system with accompanying beneficial effects such as inhibition of pro-inflammatory cytokines in vivo and/or promotion of anti-inflammatory cytokines are administered to patients. These synthetic and semi-synthetic bodies are three dimensional bodies having shapes and dimensions ranging from those resembling mammalian cells to shapes and dimensions approximating to apoptotic bodies produced by apoptosis of mammalian cells (typically but not exclusively spheroidal, cylindrical, ellipsoidal including oblate and prolate spheroidal, serpentine, reniform, etc., and from about 50 nanometers to about 500 microns in diameter), and having phosphatidyl serine (PS) molecules on the surface thereof. Such bodies are hereinafter referred to as "PS-carrying bodies".

The term "synthetic or semi-synthetic PS-carrying bodies" refers to liposomes containing PS as well as up to 50% non-PS components of the liposomes. The term "non-liposomal synthetic bodies" refers PS-carrying bodies that are not liposomes.

As noted above, exposed PS on the membrane of a cell is known to play a key role in the clearance of apoptotic lymphocytes by macrophages. A receptor for PS is present on macrophages. A "phosphatidylserine receptor" or "PS receptor" is a receptor on an antigen presenting cell (APC), such as a macrophage, whose activity is blocked by soluble phosphatidylserine, either monomeric or oligomeric. It is contemplated that the PS receptor may also be present on other APCs, such as dendritic cells and B cells. It is understood that PS is a ligand of the PS receptor.

According to this invention, PS-carrying bodies interact with a patient's immune system, after administration to the patient by suitable means, presumably by engulfment by or other interaction with macrophages and/or dendritic cells or other antigen-presenting cells, to give substantially similar effects in terms of cytokine responses as are obtained when apoptotic cells/bodies are phagocytosed by macrophages.

It is also significant that, in the present invention, PS-carrying bodies are acting as modifiers of the patient's immune system, in a manner somewhat similar to that of a vaccine. Accordingly, they are used in quantities and by administration methods to provide a sufficient localized concentration of the PS-carrying bodies at the site of injection to initiate the appropriate immune response. Quantities of PS-carrying bodies appropriate for immune system modifying substances are generally not directly correlated with body size of the recipient animal and can, therefore, be clearly distinguished from drug dosages, which are designed to provide therapeutic levels of active substances in a patient's bloodstream and tissues. Drug dosages and are accordingly very much larger.

It is contemplated that the patient may be a mammal, including but not limited to, humans and domestic animals such as cows, horses, pigs, dogs, cats, and the like.

PS-carrying bodies have surface PS molecules. As a phospholipid, PS can form the membrane of a liposome, either as the sole constituent of the membrane or as a major or minor component thereof, with other phospholipids and/or membrane forming materials. Liposomes, or lipid vesicles, are sealed sacs, in the micron or sub-micron range, the walls of which consist of layers of suitable amphiphiles. They normally contain an aqueous medium. It is understood that the PS-carrying body is not limited to a liposomal structure.

Phospholipids are amphiphilic molecules (i.e. amphiphiles), meaning that the compound comprises molecules having a polar water-soluble group attached to a water-insoluble hydrocarbon chain. The amphiphiles serving as the layers of the matrix have defined polar and apolar regions. The amphiphiles can include naturally occurring lipids such as PS, phosphatidylethanolamine, phosphatidylinositol, phosphatidylcholine, cholesterol, cardiolipin, ceramides and sphingomyelin, used alone or in admixture with one another. They can be synthetic compounds such as polyoxyethylene alkylethers, polyoxyethylene alkylesters and saccharosediesters.

The present invention contemplates the use, as PS-carrying bodies, not only those liposomes having PS as a membrane constituent, but also liposomes having non-PS membrane substituents which carry on their external surface molecules of phosphoserine, either monomers or oligomers (as distinguished from phosphatidylserine), e.g., chemically attached by chemical modification of the liposome surface, making the PS available for subsequent interaction with components of the patient recipient's immune system. Because of the inclusion of phosphoserine on the surface of such molecules, they are included within the definition of PS-carrying bodies.

Preferred PS-carrying bodies used in the present invention are liposomes constituted to the extent of 50%-100% by weight of phosphatidylserine (PS), the balance being phosphatidylcholine (PC) or other such biologically acceptable phospholipid(s). More preferred are liposomes constituted by PS to the extent of 65%-90% by weight, most preferably 70%-80% by weight, with the single most preferred embodiment, on the basis of current experimental experience, being PS 75% by weight, the balance being other phospholipids such as PC. They are prepared from mixtures of the appropriate amounts of phospholipids as starting materials, by known methods.

Methods of preparing liposomes of the appropriate size are known in the art and do not form part of this invention. Reference may be made to various textbooks and literature articles on the subject, for example, the review article by Yechezkel Barenholz and Daan J. A. Chromeline, and literature cited therein, for example New, R. C. (1990), and Nassander, U. K., et al. (1990).

The diameter of the PS liposomes of the preferred embodiment of this invention is from about 50 nanometers to about 1000 nanometers, more preferably from about 50 nanometers to about 500 nanometers. Such preferred diameters will correspond to the diameters of mammalian apoptotic bodies.

Various alternatives to liposomes may be used as PS-carrying bodies in the present invention. These include particles, granules, microspheres or beads of biocompatible materials, natural or synthetic, such as polyethylene glycol, polyvinylpyrrolidone, polystyrene, etc., polysaccharides such as hydroxethyl starch, hydroxyethylcellulose, agarose and the like, as commonly used in the pharmaceutical industry. Some such suitable substances for derivatization to attach the PS and, in the case of agarose, with PS attached, are commercially available, e.g., from Polysciences, Inc., 400 Valley Road, Warrington, Pa. 18976, or from Sigma Aldrich Fine Chemicals. The beads may be solid or hollow, or filled with biocompatible material. They are modified as required so that they carry PS molecules on their surfaces.

The PS-carrying bodies may be administered to the patient by any suitable means which brings them into operative contact with active ingredients of the patient's immune system.

The PS-carrying bodies may be suspended in a pharmaceutically acceptable carrier, such as physiological sterile saline, sterile water, pyrogen-free water, isotonic saline, and phosphate buffer solutions, as well as other non-toxic compatible substances used in pharmaceutical formulations. Preferably, the PS-carrying bodies are constituted into a liquid suspension in a biocompatible liquid such as physiological saline and administered to the patient in any appropriate route which introduces it to the immune system, such as intra-arterially, intravenously or most preferably intramuscularly or subcutaneously.

It is contemplated that the PS-carrying bodies may be freeze-dried or lyophilized which may be later resuspended for administration. This invention is also directed to a kit of part comprising lyophilized or freeze-dried PS-carrying bodies and a pharmaceutically acceptable carrier, such as physiological sterile saline, sterile water, pyrogen-free water, isotonic saline, and phosphate buffer solutions, as well as other non-toxic compatible substances used in pharmaceutical formulations.

A preferred manner of administering the PS-carrying bodies to the patient is a course of injections, administered daily, several times per week, weekly or monthly to the patient, over a period ranging from a week to several months. The frequency and duration of the course of the administration is likely to vary from patient to patient, and according to the condition being treated, its severity, and whether the treatment is intended as prophylactic, therapeutic or curative. Its design and optimization is well within the skill of the attending physician.

The quantities of PS-carrying bodies to be administered will vary depending on the nature of the mammalian disorder it is intended to treat and on the identity and characteristics of the patient. It is important that the effective amount of PS-bodies is non-toxic to the patient, and is not so large as to overwhelm the immune system. When using intra-arterial, intravenous, subcutaneous or intramuscular administration of a liquid suspension of PS-carrying bodies, it is preferred to administer, for each dose, from about 0.1-50 ml of liquid, containing an amount of PS-carrying bodies generally equivalent to 10%-1000% of the number of leukocytes normally found in an equivalent volume of whole blood or the number of apoptotic bodies that can be generated from them. Generally, the number of PS-carrying bodies administered per delivery to a human patient is in the range from about 500 to about 500,000,000 (<50 ng lipid), more preferably from about 10,000 to about 10,000,000, and most preferably from about 200,000 to about 2,000,000.

Since the PS-carrying bodies are acting, in the process of the invention, as immune system modifiers, in the nature of a vaccine, the number of such bodies administered to an injection site for each administration is a more meaningful quantitation than the number or weight of PS-carrying bodies per unit of patient body weight. For the same reason, it is now contemplated that effective amounts or numbers of PS-carrying bodies for small animal use may not directly translate into effective amounts for larger mammals on a weight ratio basis.

While it is not intended that the scope of the present invention should be limited by any particular theories of its mode of operation, the following is offered as a tentative explanation, for a better understanding of the ways and means by which the invention may be put into practice. It is postulated that antigen-presenting cells of the patient's immune system, notably professional antigen presenting cells (APCs) including macrophages and dendritic cells, take up the PS-carrying bodies in a similar manner to the way in which they would take up apoptotic cells and apoptotic bodies. Having taken up the PS-carrying bodies, the APCs induce an anti-inflammatory response promoting a change in the Th cell population with an increase in the proportion of Th2 cells and/or other regulatory/anti-inflammatory cell populations (e.g., Tr1 cells), and a decrease in Th1 cells. Th2 cells and other regulatory cells secrete anti-inflammatory cytokines such as interleukin-10, leading to reduced inflammation.

The present invention is indicated for use in prophylaxis and/or treatment of a wide variety of mammalian disorders where T-cell function, inflammation, endothelial dysfunction and inappropriate cytokine expression are involved. A patient having or suspected of having such a disorder may be selected for treatment. "Treatment" refers to a reduction of symptoms, such as, but not limited to, a decrease in the severity or number of symptoms of the particular disease or to limit further progression of symptoms.

With respect to T-cell function (T-cell mediated) disorders, these may be autoimmune disorders including, but not limited to diabetes, scleroderma, psoriasis and rheumatoid arthritis.

The invention is indicated for use with inflammatory allergic reactions, organ and cell transplantation reaction disorders, and microbial infections giving rise to inflammatory reactions. It is also indicated for use in prophylaxis against oxidative stress and/or ischemia reperfusion injury, ingestion of poisons, exposure to toxic chemicals, radiation damage, and exposure to airborne and water-borne irritant substances, etc., which cause damaging inflammation. It is also indicated for inflammatory, allergic and T-cell-mediated disorders of internal organs such as kidney, lever, heart, etc.

With respect to disorders involving inappropriate cytokine expression for which the present invention is indicated, these include neurodegenerative diseases. Neurodegenerative diseases, including Down's syndrome, Alzheimer's disease and Parkinson's disease, are associated with increased levels of certain cytokines, including interleukin-1β (IL-1β) (see Griffin W S T et al. (1989); Mogi M. et al. (1996)). It has also been shown that I1-1β inhibits long-term potentiation in the hippocampus (Murray, C. A. et al. (1998)). Long-term potentiation in the hippocampus is a form of synaptic plasticity and is generally considered to be an appropriate model for memory and learning (Bliss, T. V. P. et al. (1993)). Thus, inappropriate cytokine expression in the brain is currently believed to be involved in the development and progression of neurodegenerative diseases.

Thus, the invention is indicated for the treatment and prophylaxis of a wide variety of mammalian neurodegenerative and other neurological disorders, including Downs syndrome, Alzheimer's disease, Parkinson's disease, senile dementia, depression, multiple sclerosis, Huntingdon's disease, peripheral neuropathies, spinal cord diseases, neuropathic joint diseases, chronic inflammatory demyelinating disease, neuropathies including mononeuropathy, polyneuropathy, symmetrical distal sensory neuropathy, neuromuscular junction disorders, myasthenias and amyotrophic lateral sclerosis (ALS).

Regarding disorders involving endothelial dysfunction, the present invention is indicated for the treatment and prophylaxis of a wide variety of such mammalian disorders including, but not limited to, cardiovascular diseases, such as atherosclerosis, peripheral arterial or arterial occlusive disease, congestive heart failure, cerebrovascular disease (stroke), myocardial infarction, angina, hypertension, etc., vasospastic disorders such as Raynaud's disease, cardiac syndrome X, migraine etc., and the damage resulting from ischemia (ischemic injury or ischemia-reperfusion injury). In summary, it can be substantially any disorder that results from an inappropriately functioning endothelium.

EXAMPLES 1-5

These examples show the effect of injecting various phosphatidylserine-containing liposomes of various sizes and compositions, and in various concentrations, on ear swelling in the murine contact hypersensitivity (CHS) model, a Th1-mediated inflammatory reaction, an art-accepted model. For these experiments, female BALB/c mice (Jackson Laboratories) age 6-8 weeks and weighing 22-25 g were used.

Example 1

PS Liposomes

Phosophatidylserine (PS) containing liposomes of size 100±20 nanometers were prepared as described above which had a phosphatidylserine content of 100% (i.e. made entirely of PS). A stock suspension of liposomes containing $4.8 \times 10^{14}$ liposomes per ml was diluted with PBS to give an injection suspension containing $6 \times 10^6$ particles per ml, and each animal was injected with 50 μl of this suspension, containing $3 \times 10^5$ liposomes.

Protocol

Test group A which received the liposomes comprised 25 animals in number. Control group comprised 24 animals. The following experiments were run:

TABLE 1

| Group | Day 1 | Day 2 | Day 3 | Day 4 | Day 5 | Day 6 | Day 7 (24 hours) |
|---|---|---|---|---|---|---|---|
| A 100% PS | Inject then sensitize | Inject sensitized | Inject | Inject | Inject | Inject | Inject then challenge | Ear measured |
| Positive control (untreated animals) | | | | | | challenge | Ear measured |

On Days 1-6, mice of Group A were injected with liposomes prepared from 100% PS. Liposomes were injected in 50 µl volume via intramuscular (IM) injection, i.e. 300,000 liposomes per injection, for a total administration over the test period of 1,800,000 liposomes. Mice of the control group received no liposomes, but were sensitized, challenged and tested in the same way as mice of group A, as described below.

Sensitization

Day 1, following liposome injection for that day, mice were anesthetized using 0.2 ml intraperitoneal (IP) injection of 5 mg/ml pentobarbital sodium. The abdominal skin of the mouse was sprayed with 70% ETOH. A blade was used to remove about a one-inch diameter of hair from the abdomen. The bare area was painted with 25 µl of 0.5% 2,4-dinitrofluorobenzene (DNFB) in 4:1 acetone:olive oil using a pipette tip.

Day 6, following liposome injection for that day, mice were challenged with DNFB as follows: 10 µl of 0.2% DNFB was painted on the dorsal surface of the right ear with a pipette tip and 10 µl of vehicle was painted on the left ear with a pipette tip.

Results

Figure 1:
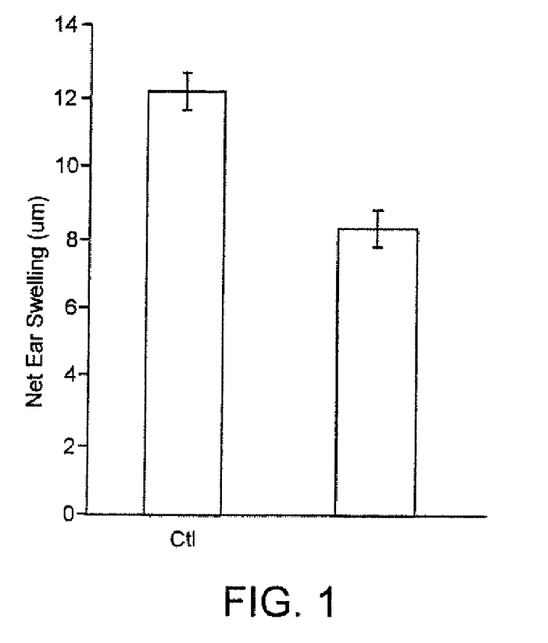
FIG. 1 shows net ear swelling (microns) in control and treated mice using the murine contact hypersensitivity (CHS) model.

On Day 7, 24 hours after challenge, each animal was anesthetized with Halothane, and ear thickness (in microns) was measured using a Peacock spring loaded micrometer. Increase in ear swelling is used as a measure of CHS response. Data is expressed as the difference in the treated right ear thickness minus the thickness of the vehicle treated left ear. The significance of difference between the two experimental groups is determined by the two-tailed student test. A value of p<0.05 is considered significant. The results are presented below, and are also presented graphically on accompanying FIG. 1, a bar graph of ear swelling, in microns.

| Group | Control | A |
|---|---|---|
| Mean ear swelling (microns) | 10.75 | 8.52 |
| Standard deviation | 3.03 | 2.77 |
| Standard error | 0.62 | 0.55 |
| P vs. control | | <0.01 |
| % inhibition v.s. control | | 20.70 |

Example 2

Liposomes of size 100±20 nanometers and containing different amounts of phosphatidyl serine, namely 90%; 75% and 50%, with the remainder being phosphatidylcholine (PC), were prepared as described, from starting mixtures of the appropriate relative quantities of the respective phospholipids. Using 4 different groups of animals, five mice per group, the following experiments were run.

| Group | Day 1 | Day 2 | Day 3 | Day 4 | Day 5 | Day 6 | Day 7 (24 hours) |
|---|---|---|---|---|---|---|---|
| B 90% PS | Inject then sensitize | Inject | Inject | Inject | Inject | Inject then challenge | Ear measured |
| C 75% PS | Inject then sensitize | Inject | Inject | Inject | Inject | Inject then challenge | Ear measured |
| D 50% PS | Inject then sensitize | Inject | Inject | Inject | Inject | Inject the challenge | Ear measured |
| Positive control (untreated animals) | senstized | | | | | challenged | Ear measured |

The amounts and procedure for injection, the sensitization procedure, the challenge procedure and the results measurements were all as described in Example 1.

Figure 2:
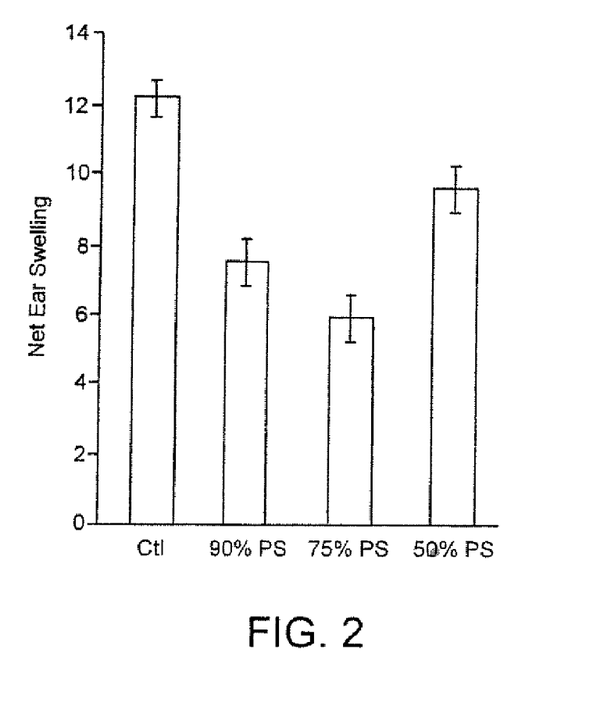
FIG. 2 shows net ear swelling in control and treated mice in the CHS model where mice were treated with PS liposomes where the amount of PS in the liposome was varied.

The results are given below, in Table 2, and are graphically presented on FIG. 2. They show an apparent optimum PS concentration in the liposome of about 75% by weight.

TABLE 2

| Group | B | C | D | Control |
|---|---|---|---|---|
| % PS Liposome | 90 | 75 | 50 | — |
| Mean swelling | 7.33 | 5.53 | 6.87 | 10.43 |
| Standard deviation | 2.50 | 3.60 | 2.26 | 3.32 |
| Standard error | 0.67 | 0.96 | 0.60 | 0.86 |
| P vs. control | 0.00829 | 0.000757 | 0.002135 | |
| % inhibiton vs. control | 29.7 | 47 | 34.1 | |

Example 3

Figure 3:
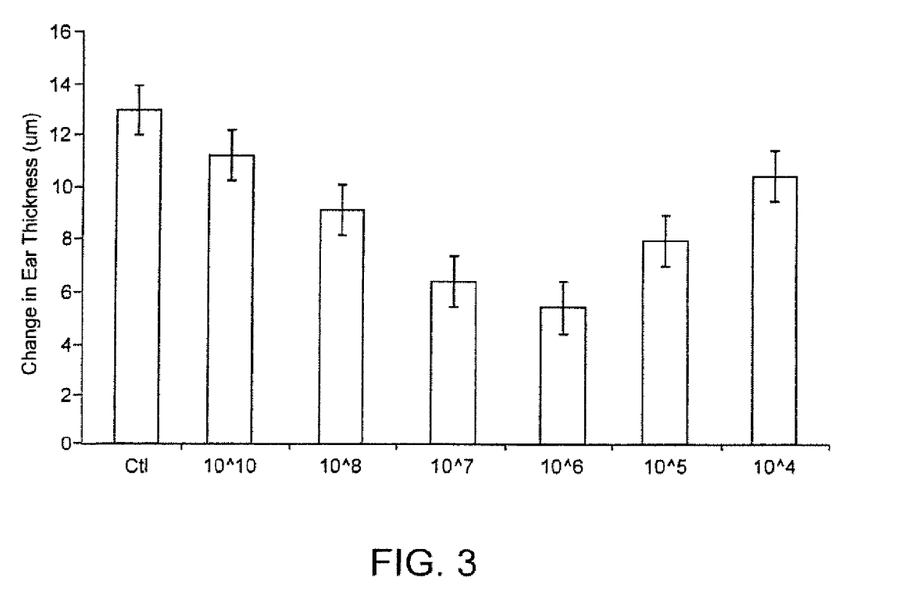
FIG. 3 shows the change in ear swelling in control and treated mice where mice were treated with varying numbers of liposomes using the CHS model.

Again using the CHS murine model described above, liposomes of size 100±20 nanometers and containing 75% PS and 25% PC were injected into groups of mice according to the same protocol but at different dosage amounts i.e. different numbers of liposomes in each 50 µl injection. The numbers of liposomes per ml for the respective groups of animals, and the results obtained, using the same test and measurement procedures, were as follows:

Group E-$10^{10}$ (10 animals) average net ear swelling 11.10; SD 2.56; SE 0.81;
% of control 86; % reduction 14;
p vs. control 0.052
Group F-$10^8$ (15 animals) average net ear swelling 8.93; SD 2.49; SE 0.64;
% of control 68; % reduction 32;
p vs. control <0.0001
Group G-$10^7$ (5 animals) average net ear swelling 6.20; SD 1.92; SE 0.86;
% of control 48; % reduction 52;
p vs. control <0.0001
Group H-$10^6$(15 animals) average net ear swelling 5.13; SD 2.17; SE 0.56;
% of control 40; % reduction 60;

p vs. control <0.0001
Group J-10$^5$ (5 animals) average net ear swelling 7.60; SD 1.52; SE 0.68;
% of control 59; % reduction 41;
p vs. control <0.0001
Group K-10$^4$ (10 animals) average net ear swelling 10.0; SD 1.05; SE 0.33;
% of control 78; % reduction 22;
p vs. control 0.000128.
These results are presented graphically on FIG. 3

Example 4

Liposomes of 100% PS of various sizes were prepared, and injected into groups of mice according to the protocol described in Example 1. The volumes of injection, numbers of liposomes per injection, procedures and measurements were also as described in Example 1.
The results obtained were as follows:

| Group (3 animals each) | Liposome size (nm) | Average ear swelling, % of control | SD | SE |
|---|---|---|---|---|
| L | 50 | 23 | 1.00 | 0.45 |
| M | 100 | 28 | 2.00 | 0.89 |
| N | 400 | 25 | 5.13 | 2.29 |

Figure 4:
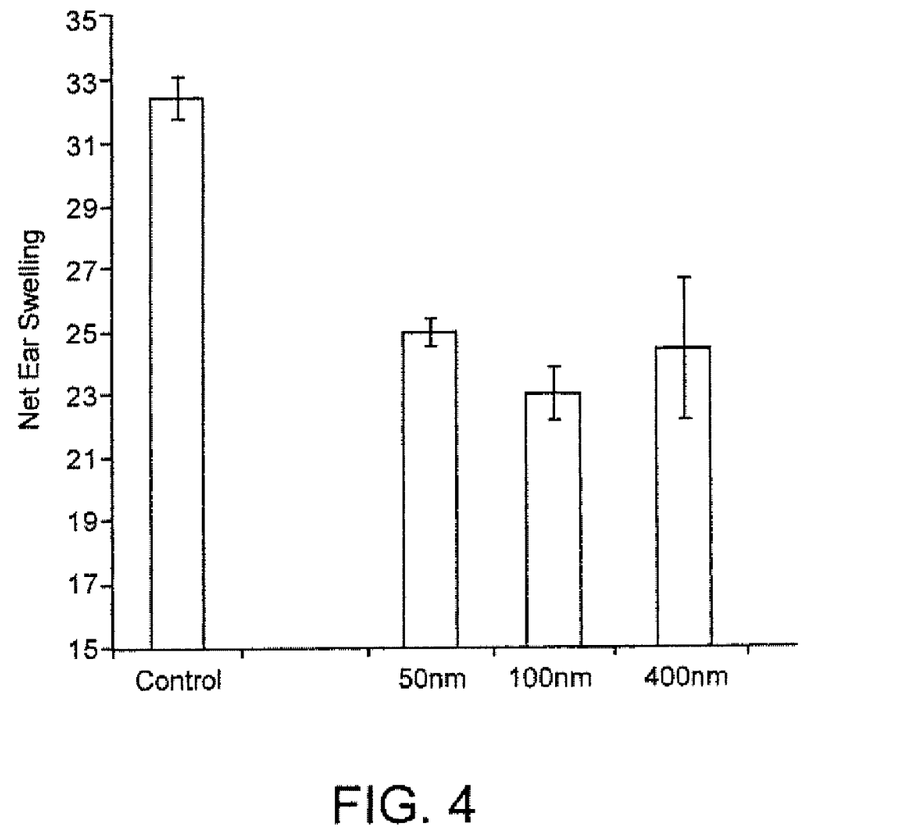
FIG. 4 shows the change in ear swelling in control and treated mice where mice were treated with varying sizes of PS-containing liposomes using the CHS model.

These results are presented graphically on accompanying FIG. 4. The liposomes are of fairly uniform size, with an approximate size range of ±20 nm.

Example 5

Figure 5:
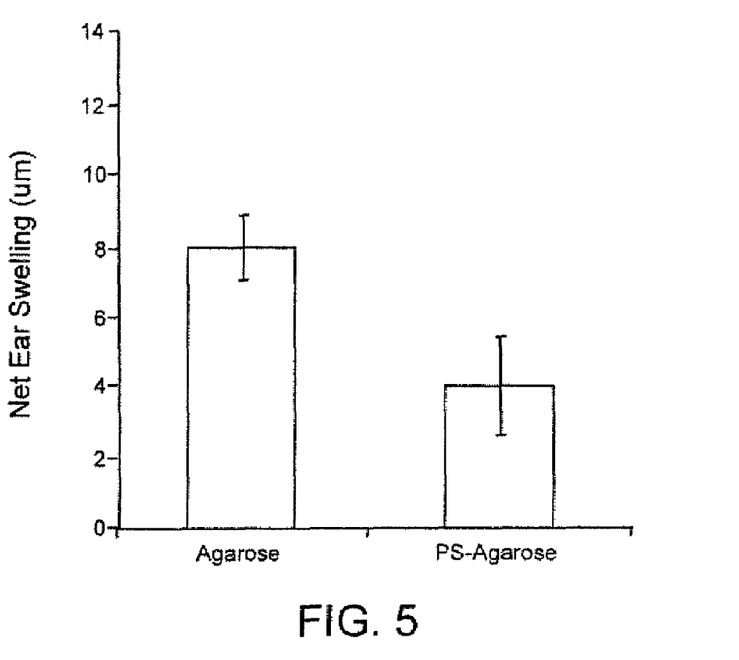
FIG. 5 shows the change in ear swelling in control and treated mice using the CHS model where agarose beads derivatized to carry PS on their surface were administered.

Agarose beads derivatized to carry phosphatidylserine PS on their surfaces were used in the murine contact hypersensitivity model described in Example 1, in place of the liposomes. The agarose beads were characterized by an average particle size of 45 -165 microns and generally spherical in size (Sigma Aldrich Fine Chemical, Catalogue no. P3578). As a control, similar agarose beads free of PS were used (Sigma Aldrich Fine Chemical, Catalogue no. A9045). Both the derivatized and the non-derivatized beads are commercially available from Sigma Chemical Co.
The agarose beads were suspended in PBS, and injected into the animals at a dosage of 300,000 beads, in 50 µl of suspension for each injection, according to the procedures and protocol described in Example 1. Measurements of ear swelling were taken as described. Five animals were used, in each of the experimental group and the control group.
Whereas the animals receiving underivatized agarose showed a mean net change in ear thickness as a result of the experiment of 7.8 um (SD 2.17, SEM 0.97), the corresponding number for the animals receiving PS-derivatized beads was 4.00 (SD 2.92, SEM 1.30, p vs. agarose 0.047509), indicating significant activity of PS when attached to solid beads in accordance with the invention, as well as liposomal forms thereof. The results are presented graphically in FIG. 5.

Example 6

Figure 6:
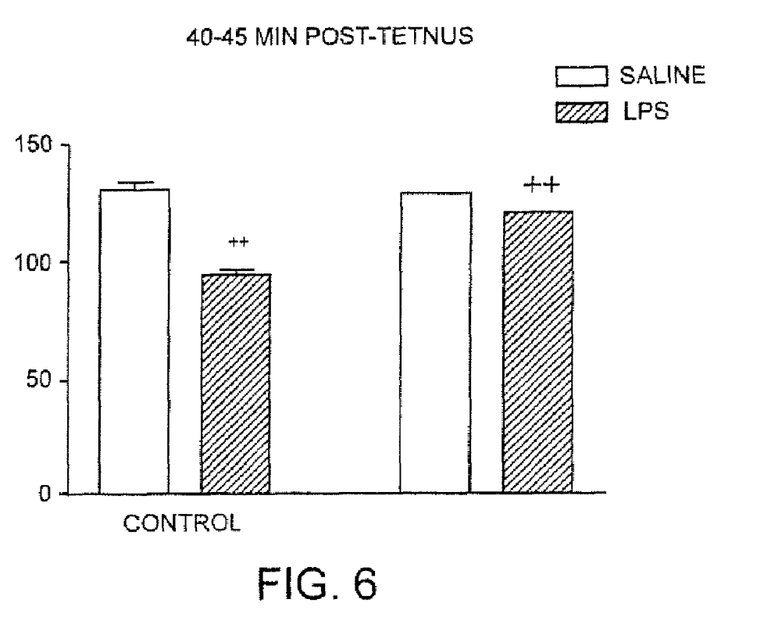
FIG. 6 is a bar graph showing the excitatory post-synaptic potential (epsp) slope (%) in control and treated rats using the Long-Term Potentiation (LTP) animal model.
Figure 7:
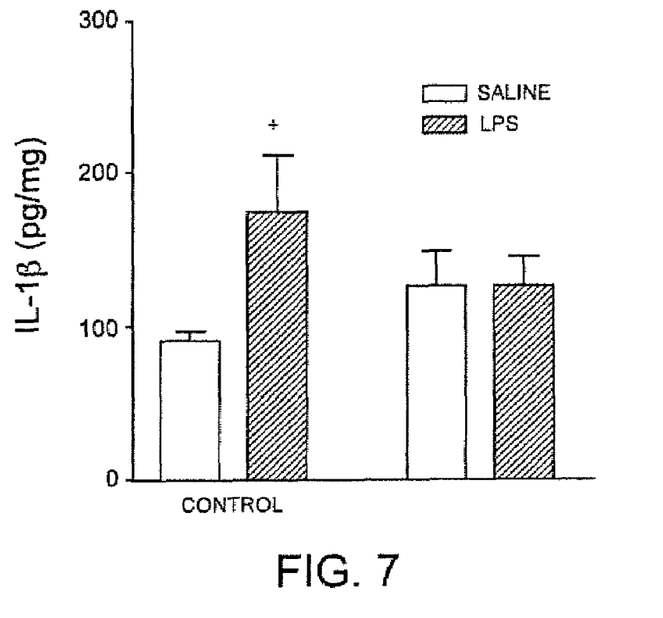
FIG. 7 shows the concentration of IL-1β. in the hippocampus of control and treated rats.

The hippocampus of the brain has been identified as a brain area which is especially vulnerable in degenerative conditions associated with cognitive dysfunction, such as Alzheimer's disease. In order to study the cellular and molecular mechanisms underlying cognitive function, the Long-Term Potentiation (LTP) animal model is used. LTP is a form of synaptic plasticity that occurs in the hippocampal formation which has been proposed as a biological substrate for learning and memory (Bliss et al, Nature 361:31-39 (1990)). Flectrophysiology recording of LTP in rats in vivo followed by analysis of biochemical changes in hippocampal tissue harvested following recording provides a model which permits investigation of how the cellular events that underlie LTP may be altered in states associated with neuroinflammation such as aging, stress, Alzheimer's disease, and bacterial infection.
Systemic administration of lipopolysaccharide (LPS), a component of the cell wall of Gram-negative bacteria, provokes an activation of the immune system by inducing an increase in pro-inflammatory cytokines such as IL-1β. One example of a neuronal deficit induced by LPS and IL-1β. is the impairment of long term potentiation (LTP) in the hippocampus. An indicator of LTP is the mean slope of the population excitatory post-synaptic potential (epsp). Upon tetanic stimulation, the epsp slope (%) rises sharply indicating increased synaptic activity, but LPS-induced inhibition of LTP lessens this rise, and/or causes the epsp slope to revert more rapidly to base line, indicating that the increased sypnaptic activity is short-lived. Accordingly measurements of the epsp slope (%) at timed intervals after tetanic stimulation can be used to reflect memory and the loss thereof following an inflammatory stimulus as well as inflammation in the hippocampus of the brain.
Protocol
LTP: 6 groups of 8 Male Wistar rats (c.300 g) were injected intramuscularly with saline carrier alone or with PS bodies, namely liposomes of 100% PS, size 100±20 nanometers in saline carrier. 9×10$^5$ liposomes in 150 ul of saline were injected into the rats on days-14, -13, and -1.
On day 0, rats were anesthetized with urethane (1.5 mg/kg, ip) and injected with LPS (lipopolysaccharide) (100 mg/kg i.p.) or saline as a control. After three hours, a bipolar stimulating electrode and a unipolar recording electrode were implanted in the perforant path and in the dorsal cell body of the deritate gyrus respectively. 0.033 Hz test shocks were given and responses recorded for 10 minutes before and 45 minutes after tetanic stimulation (3 trains of stimuli delivered at 30 sec. intervals, 250 Hz for 200 ms) to induce LPS.
The rats were killed by decapitation; the hippocampus, the tetanized and untetanized dentate gyri, the cortex and entorhinal cortex were dissected on ice, cross-chopped into slices and frozen in 1 ml of Krebs solution containing 10% DMSO.
Effectiveness of blocking LPS-induced inhibition of LTP was assessed from the electrophysiological recordings of neurotransmitter release in the tissue. The epsp slope (%) was followed for 10 minutes before and 40 minutes after tetanic stimulation. Tissue from animals which had received a course of pretreatment with PS liposomes and an injection of LPS exhibited a decline in epsp slope (%) of less than 5% at 40 to 45 minutes after tetanic stimulation, whereas tissue from similarly injected animals without the PS liposome pretreatment course showed an approximate 25% reduction over the same period. This is a clear indication the described pretreatment with PS liposomes is exerting a neuroprotective effect. This is shown in FIG. 6, bar graphs of epsp slope (%) of LPS-injected, pretreated animal tissues (right hand side) and LPS-injected, non-pretreated animal tissues (left hand side), at 40-45 minutes from tetanic stimulation). The ** notation indicates significant difference from the respective saline control. The ++ notation indicates significant difference from the LPS injected, non-pre-conditioned control.
In addition, IL-1β concentration in the hippocampus was measured, by enzyme-linked immunosorbent assay techniques known in the art. The results are shown in FIG. 7, bar graphs of IL-1β in pg/mg for control tissues which received no pretreatment with PS liposomes (left hand side) and tissues which received the pre-treatment described above (right hand side). The shaded bars represent results from tissues of animals given an LPS injection, the clear bars those which received no such injection. It is clear that the preconditioning treatment has effectively inhibited the up-regulation of the inflammatory cytokine IL-1β ordinarily resulting from LPS injection.

Figure 8:
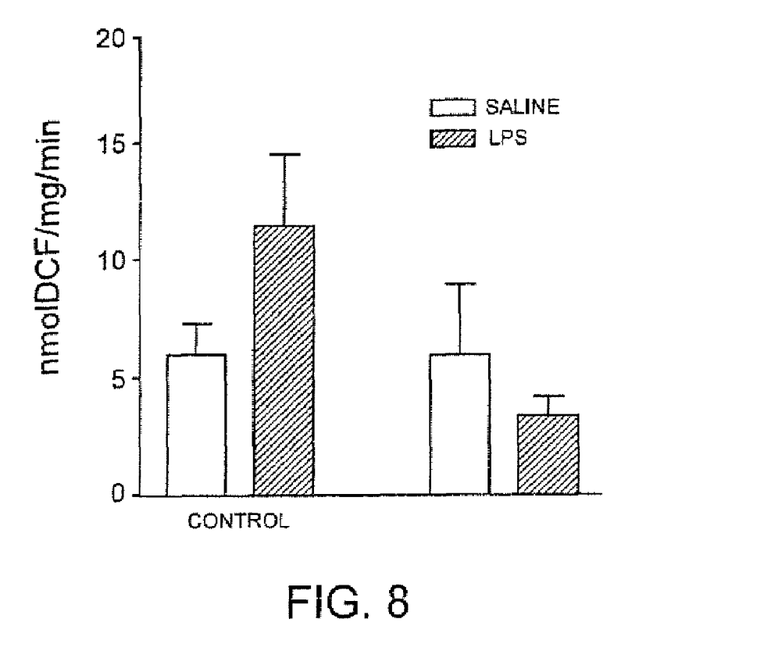
FIG. 8 shows reactive oxygen species (ROS) formation in the hippocampus of control and treated rats.

Similarly, reactive oxygen species (ROS) formation in the hippocampus was investigated. ROS was assessed in synaptosomes prepared from hippocampus by measuring DCF, the oxidized fluorescent product of DCFH-DA. ROS are known to destroy nerve cells. These results are similarly presented in FIG. 8, again demonstrating the neuroprotective effect of the process of the present invention.

Figure 9:
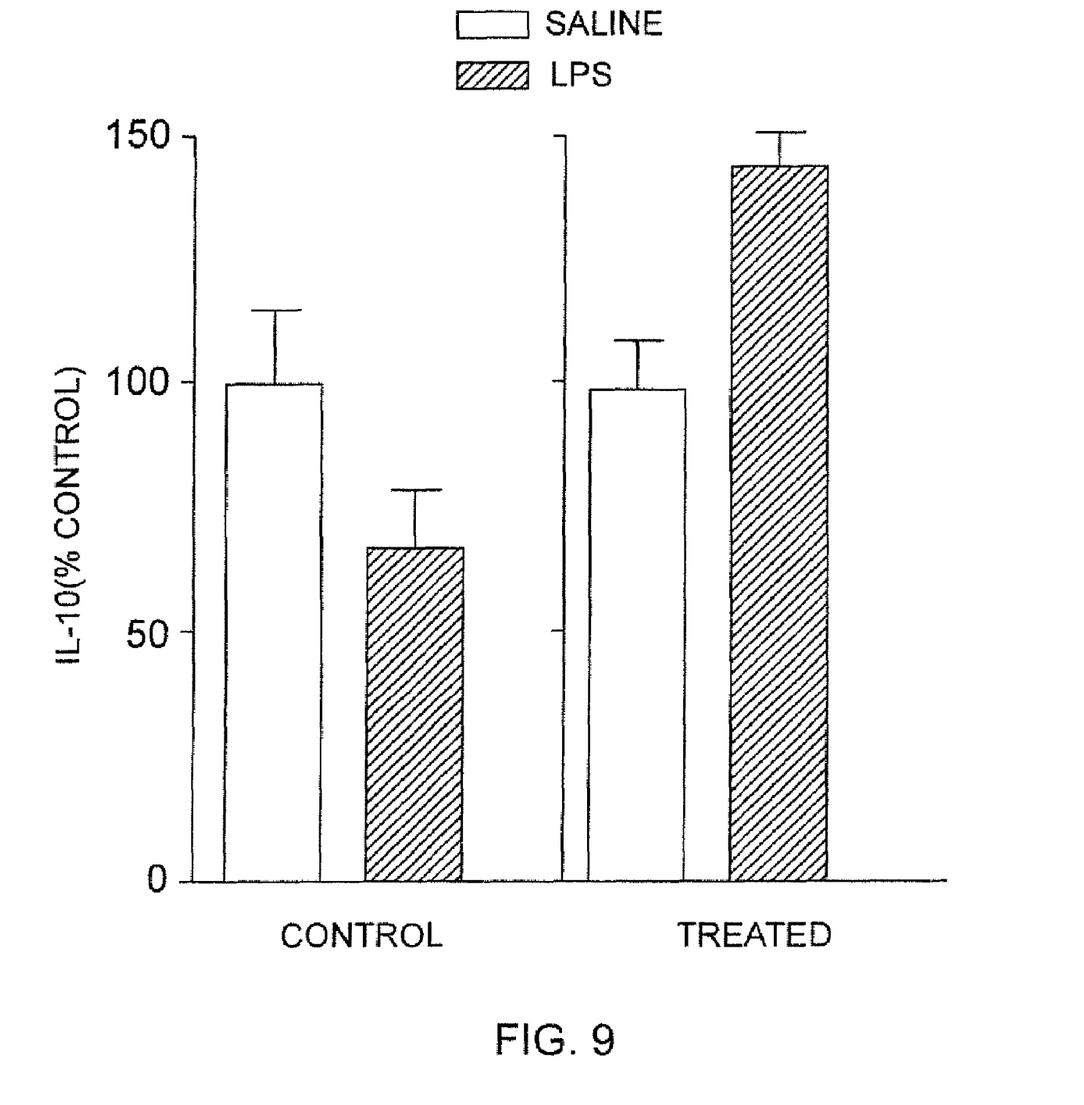
FIG. 9 shows the concentration of IL-10 in the hippocampus of control and treated rats.

Further, the concentration of the anti-inflammatory cytokine IL-10 in the hippocampus was measured. IL-10 concentration was measured by enzyme-linked immunosorbent assay, and expressed as a percentage difference from the control. These results are presented, in a similar manner as FIGS. 7 and 8, in FIG. 9. They show that, in tissue from animals which had not received pre-treatment according to the invention, LPS injection caused a reduction in IL-10 content of about 30% (left side bars) as compared with saline injection. In contrast, in tissue from animals subjected to the course of pre-treatment with PS liposomes as described, LPS treatment caused an increase of about 45% in the IL-10 content as compared with saline injection (right side bars).

These results on IL-10 and IL-1β contents indicate significant anti-inflammatory effects in the hippocampus, following pre-treatment in accordance with the present invention:

In summary, the results show that PS-carrying bodies are effective to block LPS-induced LTP inhibition and neuroinflammation.

All publications, patents and patent applications previously cited above are herein incorporated by reference in their entirety.

What is claimed is:

1. A unit dosage form comprising a pharmaceutically acceptable carrier and synthetic or semi-synthetic phosphatidylserine (PS)-carrying bodies in an amount from about 500 to about 500,000,000 per unit of administration.

2. The unit dosage form of claim 1, wherein at least a portion of the PS-carrying bodies have a conformation and size corresponding to mammalian apoptotic bodies, wherein the surface of said bodies have been modified to contain a plurality of ligands for one or more phosphatidylserine receptors; which bodies are capable of binding to a phosphatidylserine receptor on an antigen presenting cell when administered to a mammalian patient.

3. The unit dosage form of claim 1, comprising the PS-carrying bodies in an amount from about 10,000 to about 10,000,000 per unit of administration.

4. The unit dosage form of claim 3, comprising the PS-carrying bodies in an amount from about 200,000 to about 2,000,000 per unit of administration.

5. The unit dosage form of claim 1, wherein the synthetic or semi-synthetic PS-carrying bodies are liposomal synthetic bodies.

* * * * *